United States Patent [19]

Bally et al.

[11] Patent Number: 5,409,704
[45] Date of Patent: *Apr. 25, 1995

[54] LIPOSOMES COMPRISING AMINOGLYCOSIDE PHOSPHATES AND METHODS OF PRODUCTION AND USE

[75] Inventors: Marcel B. Bally, Vancouver, Canada; Lois E. Bolcsak, Lawrenceville, N.J.; Pieter R. Cullis, Vancouver, Canada; Andrew S. Janoff, Yardley, Pa.; Lawrence D. Mayer, Vancouver, Canada

[73] Assignee: The Liposome Company, Inc., Princeton, N.J.

[*] Notice: The portion of the term of this patent subsequent to Dec. 4, 2007 has been disclaimed.

[21] Appl. No.: 59,192

[22] Filed: May 6, 1993

Related U.S. Application Data

[63] Continuation of Ser. No. 537,160, May 15, 1990, abandoned, which is a continuation of Ser. No. 946,391, Dec. 23, 1986, abandoned, which is a continuation-in-part of Ser. No. 800,545, Nov. 21, 1985, abandoned, which is a continuation-in-part of Ser. No. 752,423, Jul. 5, 1985, abandoned, which is a continuation-in-part of Ser. No. 749,161, Jun. 26, 1985, abandoned.

[51] Int. Cl.$^6$ ............ A61K 9/127; A61K 9/133
[52] U.S. Cl. ............ 424/450; 264/4.1; 264/4.3; 428/402.2; 514/37; 514/78; 514/912; 514/913; 514/914
[58] Field of Search ........... 264/4.1, 4.3; 428/402.2; 514/78, 912, 913, 914, 915; 424/450; 436/829

[56] References Cited

U.S. PATENT DOCUMENTS

| | | |
|---|---|---|
| 498,268 | 5/1883 | Janoff et al. . |
| 604,503 | 5/1884 | Janoff et al. . |
| 782,814 | 10/1885 | Pidgeon . |
| 3,962,429 | 6/1976 | Furuno et al. .......... 514/41 |
| 3,993,754 | 11/1976 | Rahman et al. ......... 424/450 X |
| 4,016,100 | 4/1977 | Suzuki et al. .......... 264/4.3 |
| 4,089,801 | 5/1978 | Schneider ............ 264/4,3 |
| 4,145,410 | 3/1979 | Sears ............... 424/450 |
| 4,193,983 | 3/1980 | Ullman et al. .......... 424/450 X |
| 4,217,344 | 8/1980 | Vanlerberghe et al. ..... 428/402.2 X |
| 4,224,179 | 9/1980 | Schneider ............ 264/4.6 |
| 4,235,871 | 11/1980 | Papahadjopoulos et al. ... 424/450 X |
| 4,241,046 | 12/1980 | Papahadjopoulos et al. ... 424/450 X |
| 4,370,349 | 1/1983 | Evans et al. ........... 264/4.1 X |
| 4,372,949 | 2/1983 | Kodama et al. ......... 424/450 X |
| 4,389,330 | 6/1983 | Tice et al. ............ 264/4.1 |
| 4,394,372 | 7/1983 | Taylor ............... 424/85.4 |

(List continued on next page.)

FOREIGN PATENT DOCUMENTS

| | | | |
|---|---|---|---|
| 30260/71 | 4/1973 | Australia . | |
| 59-210013 | 11/1984 | Japan | ........ A61K 9/10 |
| 60-80767 | 5/1985 | Japan . | |
| 2134869 | 8/1984 | United Kingdom . | |
| 1123697 | 11/1984 | U.S.S.R. | ........ A61K 9/00 |
| 83/03383 | 10/1983 | WIPO . | |
| 85/00515 | 2/1985 | WIPO | ........ A61K 9/50 |
| 85/00751 | 2/1985 | WIPO . | |
| 85/05030 | 11/1985 | WIPO . | |

OTHER PUBLICATIONS

*Liposomes,* Edited by Marc. J. Ostro, Marcel Dekker, Inc., New York (1983) pp. 70 & 71.

*Cecil Textbook of Medicine,* 16th Edition, vol. 2, Edited by J. B. Wyngaarden et al., W. B. Saunders Co., Philadelphia (1982), pp. 1432–1435.

Alexander, et al., "Interaction of Aminoglycoside Antibodies with Phospholipid Liposomes Studies by Microelectrophoresis", J. Antibio., 32:504–10 (1979).

Au, et al., "Membrane Perturbation by Aminoglyco- (List continued on next page.)

*Primary Examiner*—Richard D. Lovering
*Attorney, Agent, or Firm*—Kenneth B. Rubin

[57] ABSTRACT

Aminoglycosides, analogs and derivatives thereof, in the form of phosphate salts are described as well as the process for making and utilizing same. Aminoglycoside phosphate liposomes and nonguanadino aminoglycoside phosphate liposomes, their preparation and use, are particularly described.

17 Claims, 3 Drawing Sheets

U.S. PATENT DOCUMENTS

| | | | |
|---|---|---|---|
| 4,397,846 | 8/1983 | Weiner et al. | 514/104 |
| 4,411,894 | 10/1983 | Schrank et al. | 514/78 X |
| 4,421,741 | 12/1983 | Gilbert et al. | 514/39 |
| 4,455,296 | 6/1984 | Hansen et al. | 424/87 |
| 4,460,577 | 7/1984 | Moro et al. | 424/450 |
| 4,485,045 | 11/1984 | Regen | 264/4.3 X |
| 4,515,736 | 5/1985 | Deamer | 264/4.3 |
| 4,522,803 | 6/1985 | Lenk et al. | 428/402.2 X |
| 4,529,561 | 7/1985 | Hunt et al. | 264/4.3 |
| 4,532,089 | 7/1985 | MacDonald | 436/829 X |
| 4,588,578 | 5/1986 | Fountain et al. | 424/1.1 |
| 4,610,868 | 9/1986 | Fountain et al. | 424/1.1 |
| 4,731,210 | 3/1988 | Weder et al. | 264/4.3 |
| 4,897,384 | 1/1990 | Janoff et al. | 514/34 |
| 4,975,282 | 12/1990 | Cullis et al. | 424/450 |
| 5,030,453 | 7/1991 | Lenk et al. | 424/450 |
| 5,059,591 | 10/1991 | Janoff et al. | 514/31 |

OTHER PUBLICATIONS sides as a Simple Screen of their Toxicity", Antimicrobial Agents and Chemotherapy, 30:395–397 (1986).

Barza, et al., "Pharmacokinetics of subconjunctival Liposome–Encapsulated Gentamicin in Normal Rabbit Eyes", Investigative Ophthlmology & Visual Science, 25: 486–90 (1984).

Carlier, et al., "Inhibition of Lysosomal Phospholipases by Aminoglycoside Antibiotics: In Vitro Comparative Studoies":, Antimicrobial Agents and Chemotherapy, 30: 395–397 (1986).

Chung, et al., "Interaction of Gentamcin and Spermine with Bilayer membranes Containing Negatively Charged Phospholipids", Biochemistry, 24:442–452 (1985).

Dees, et al., :Enhanced Intraphagocytic Killing of *Brucella Abortus* in Bovine Mononuclear Cells by Liposomes Containing Gentamicin:, Vet. Immunology & Innumophatology 8:171–182 (1985).

Dees, et al. :Evidence for Long Term Survival of Gentamicin in Phagocytic Cells after Insertion by Liposomes, Fed. Proc., 42: Abst 3341 (1983).

Fishmann, et., :"Intravitreal Liposome–Encapsulated Gentamicin in a Rabbit Model", Investigative Ophthalmology & Visual Science, 27: 1103–6 (1986).

Fountain et al: "Treatment of *Brucella canis* and *Brucella abortus* in vitro and in vivo by stable plurilamellar vesicle–encapsulated aminoglycosides", & J. Infect. Dis. 1985, 152(3), 529–35.Chemical Abstracts, vol. 103, No. 20, 18th Nov. 1985, p. 368, abstract No. 166095e, Columbus, Ohio, US.

Kaloyanides, et al., "Adsorption of Gentamicin to Liposomes Containing Anionic Phospholipids", Fed. Proc., 42:Abst 3423 (1983).

Kubo, et al., "Binding of Propranolol and Gentamicin to Small Unilamellar Phospholipid Vesicles", Biochemical Pharmacology, 35: 3716–3765 (1986).

*Liposomes,* ed. Marc J. Ostro, Marcel Dekker, Inc., New York, (1983), pp. 70–71.

Morgan, et al., "Preparation and Properties of Liposome–Associated Gentamicin", Antomicrobial Agents and Chemotherapy, 17:544–548 (1986).

Nagy, et al., "Study in the Subconjunctival Application of Liposomes–Encapsulated Tobramycin", Ann. Immunol. Hung, 25:355–363 (1985).

*The Merck Index,* Tenth Eddition, Merck & Co., Inc., Rahway, N.J. 1983, p. 1263.

Vladimirskii et al: "Liposome preparations of streptomycin and dihydrostreptomycin", & Antibiotiki (Moscow) 1984, 29(3), 163–6, Chemical Abstracts, vol. 101, No. 2, 9th Jul. 1984, p. 294, abstract No. 12083w, Columbus, Ohio, US.

Abra, et al., 1983, Cancer Chemother. Pharmacol, 11:98, "Delivery of Therapeutic Doses of Doxorubicin in the Mouse Lung Using Lung–Accumulating Liposomes Proves Unsuccessful".

Akerman, et al., 1976, Biochim. Biophys. Acta., 426:624, "Staching of Safranine in Liposomes During Valinomycin Induced Efflux of Potassium Ions".

Bally, et al., 1985, Biochim. Biophys. Acta., 812:66, "Uptake of Saframine and Other Lipophilic Cations into Model Membrane System in Response to a Membrane Potential".

Bonventre, et al., "Killing of Intraphagocytic *Straphylococcus aureus* by Dihydrostreptomycinl Entrapped Within Liposomes", Antimicrobial Agents and Chemotherapy, 13(6), Jun. 1978, 1049–1051.

Bottcher, et al. 1961 Anal. Chim. Acta., 24:203–204, "A Rapid and Sensitive Sub–Micro Phosphorus Determination".

Brasseur, et al., "Interactions of aminoglycoside antibiotics with negatively charged lipid layers", Biochemical Pharmacology, 33(4):629–637, 1984.

Cafisco, et al., 1983, Biophys. J. 44:49, "Electrogenic

OTHER PUBLICATIONS

H+/OH— Movement Accorss Phospholipid Vesicles Measured by Spin–Labeled Hydrophobic Ions".
Chemical Abstracts 103:174355e.
Chemical Abstracts 99:49240m.
Chen, et al., 1956, Analytical Chem., 11:1756–1758, "Microdetermination of Phosphorus".
Corda, et al., J. Membr. Bio., 1982 65(3) 235–42, "Increase in Lipid Microviscosity of Unilamellar Vesicles upon the Creation of Transmembrane Potential", Chem. Abs. vol. 96, 1982, Abs. 176569p.
Crommelin, et al., 1983, Int. J. Pharm. 16(1):79 "Preparation and Characterization of Doxorubicin–Containing Liposomes: I. Influence of Liposome Charge and pH of Hydration Medium on Loading Capacity and Particle Size".
Deamer, 1983, in: Liposomes, 1983, M. Ostro (ed.), Marcel Dekker, New York pp. 26–57.
Forssen, et al., 1983, Cancer Res., 43:546, "Improved Therapeutic Benefits of Doxorubicin by Entrapment in Anionic Liposomes".
Fountain, et al., "Enhanced Intracellular Killing of *Staphylococcus aureus* by Canine Monocytess Treated with liposomes Containing Amikacin, Gentamicin, Kanamycin, and Tobramycin", Current Microbiology, 6:373–376, 1981.
Gabizon, et al., 1982, Cancer Res. 42–4734, "Liposomes as in Vivo Carriers of Adriamycin:Reduced Cardiac Uptake and Preserved Antitumor Activity in Mice".
Garcia, et al., 1983, Biochemistry 22(10):2524, "Mechanism of Lactose Translocation in Proteoliposomes Reconstituted with Iac Carrier Protein Purified from *Escherichia coli*. 1. Effect of pH and Imposed Membrane Potential on Efflux, Exchange, and Counterflow".
Gruner, et al., "Novel Multilayers Lipid Vesicles Comparison of Physical Characteristics of Multilamellar Liposomes and Stable Plurilamellar Vesicles", 1985, Biochem. 24, 2833–2842.
Hodges, et al., "The enhancement of neomycin activity on *Escherichia colis* by entrapment in liposomes", Chemical Abstracts 92, 1980, Abstr. 92:169154p.
Hope, et., 1985, Biochim. Biophys. Acta., 812:55, "Production of Large Unilamellar Vesciles by a Rapid Extrusion Procedure. Characterization of Size Distribution, Trapped Volume and Ability to Maintain a Membrane Potention".
Jonah, et al., 1975, Biochim, et Biophys. Acta 401:336–348, "Tissue Distribution of EDTA Encapsulated Within Liposomes of Varying Surface Properties".
Kano, et al., 1977, Life Sciences, 20:1729, "Enhanced Uptake of Drugs in Liposomes Use of Labile Vitamin B12 Complexes of 6–Mercaptopurine and 8–Azaguanine".
Kirby, et al., "A Simple Procedure for Preparing Liposomes Capable of high Encapsulation Efficiency Under Mild Consitions", 1984: *Liposome Technology*, G. Gregoriadis, ed. CRC PRess, Inc., vol. 1, 19–27.
Kirby, et al., 1984, Bio/Technology, 2(11):979, "Dehydration–Rehydration Vesicles: A Simple Method for High Yield Drug Entrapment in Liposomes".
Ladygina, et al., "Pharmacokinetics of Streptomycin in Mice Following the Administration of the Antibiotic's Liposomal Form", Farmatsiya (Moscow), 1984, 33(6), 38–42.
Mauk, et al., PNAS, USE 76:765, "Preparation of Lipid Vesicles Containing High Levels of Entrapped Radioactive Cations."
Mayhew et al., Biol. Cell (1981) 1983 47(1) 81–5, Chem. Abs. vol. 98, 1983, Abs. 221734t.
Mayer, et al., Chemical Abstracts 103:76141n.
Morii, et al., 1983, Int. J. Pharm. 17(2–3), 215–224, "Size and Permeability of Liposomes Extruded Through Polycarbonate Membranes."
Nichols, et al., 1976, Biochim. Biophys. Acta., 455:269, "Catecholamine Uptake and Concentration by Liposomes Maintaining pH Gradients".
Ohsawa, et al., "Fate of Lipid and Encapsulated Drug After Intramuscular Administration of Liposomes Prepared by the Freeze–Thawing Method in Rats", Chem. Pharm. Bull, 1985, 33(11): 5013–5022.
Ohsawa, et al., "Evaluation of a New Liposome Preparation Technique, the Freeze–Thawing Method, Using L–Asparaginase as a Model Drug", Chem. Pharm. Bull, 33(7) 2916–2923 (1985).
Ohsawa et al., "Improvement of Encapsulation Efficiency of Water–Soluble Drugs in Liposomes Formed by the Freeze–Thawing Method", Chem. Pharm. Bull, 1985, 33(9), 3945–3952.
Oku, et al., "Differential Effects of Alkali Metal Chlo-

OTHER PUBLICATIONS rides on Formation of Giant Liposomes by Freezing and Thawing and Dialysis", Biochem, 1983, 22(4):855–863.

Olson, et al. "Preparation of Liposomes of Defined Size Distribution by Extrusion Through Polycarbonate Membranes, 1979, BBA 557, 9–23.

Olson, Eur. J. Cancer Clin. Oncol., 18:167, "Characterization, Toxicity and Therapeutic Efficacy of Adriamycin Encapsulated in Liposomes".

Papahadjopoulos, et al, 1980, in Liposomes and Immunology, 1980, Tom and Six, eds., Elseiver, New York, "Optimization of Liposomes as a Carrier System for the Intracellular Delivery of Drugs and Macromolecules".

Pick, "Liposomes with a Large Trapping Capacity Prepared by Freezing and Thawing of Sonicated Phospholipid Mixtures", 1981, Arch. Biochem, Biophys, 212(1), 186–194.

Rahman, et a., 1982 Cancer Res. 42:1817, "Doxorubicin-Induced Chronic Cardiotoxicity and Its Protection by Lipsomal Administration".

Rosa, et al., 1982, in: Transport in Biomembranes, 1982, R. Antolini et al., (ed.), Raven Press, New York, "Liposomes Containing Doxorubicin: An Example of Drug Targeting".

Rosa, et al., 1983 Pharmacol., 26:221, "Absoprption and Tissue Distribution of Doxorubicin Entrapped in Liposomes Following Intraveous or Intraperitoneal Administration".

Shakhov, et al., 1984, Biokhimika, 48(8):1347, "Reconsitution of Highly Purified Proton-Translocating Pyrothosphatas".

Singleton, et al., 1965, J. Am Oil Chem. Soc. 42:53–56, "Chromatographically Homogeneous Lecithin from Egg Phospholipids".

Strauss, et al., "Freezing and Thawing of Liposome Suspenmsions", 1984 in *Liposome Technology,* G. Gregoriadis, ed. CRC Press, Inc., vol. 1, 197–219.

Tadakuma, et al., "Treatment of Experimental Salmonellosis in Mice with Streptomycin entrapped in Liposomes", Antimicrobial Agent and Chemotherapy, 28(1), Jul. 1985, pp. 28–82.

van Hoesel, et al., 1984, Cancer Res., 44:3698, "Reduced Cardiotoxicity and Nephrotoxicity with Preservation of Antitumor Activity of Doxorubicin Entrapped in Stable Liposomes in the LOU/MN Wsi Rat."

Vladimirskii, et al., "Pharmacokinetics of Dihydrostreptomycin After intravenous Administration of the Liposomal Preparation into Blood Serum and Tissues of intact Mice and Mice with Genralized Tuberculosis", Antibiotiki (Moscow), 1984, 29(4), 282–5.

Vladimirsky, et al., "Antibacterial Activity of Liposome-Entrapped Streptomycin in Mice Infected with Mycobacterium Tuberculosis", Biomedicine, 1982, 36, 375–377.

Vladimirskii, et al., "Efficacy of Streptomycin Incorporated into Liposomes During an Experimental Tuberculosis in the Mouse", Antibiotiki (Moscos), 1983, 28(1), 23–6.

Wang, B. "Interaction of aminoglycosidic antibiotics with mixed monolayers and liposomes of anioic and neutral phospholipids", Dissertation Abstracts International, 44(6): 1836–B, Dec. 1983.

Westman, et al., "Charge and pH Dependent Drug Binding to Model Membranes", 1982, BBA 315–328.

Hiraga et al., Chemical Abstracts, 88:121661s (1978), 2′,3′-Epiimino antibiotics.

Maier et al., Chemical Abstracts, 91:189394z (1979), Biosynthesis of streptomycin.

Kneip et al., Chemical Abstracts, 93:41177b (1980), Biosynthesis of streptomycin.

CAS Registry Handbook, 1975 Supplement, RN 55102–88–0.

CAS Registry Handbook, 1978 Supplement, RN 65982–12–9.

LIPOSOMES COMPRISING AMINOGLYCOSIDE PHOSPHATES AND METHODS OF PRODUCTION AND USE

RELATED APPLICATIONS

This application is a continuation of U.S. Ser. No. 537,160, filed May 15, 1990, now abandoned, which is a continuation of U.S. patent application Ser. No. 946,391, filed Dec. 23, 1986, and now abandoned, which is a continuation-in-part of patent application Ser. No. 800,545, filed Nov. 21, 1985, and now abandoned, which in turn is a continuation-in-part of patent application Ser. No. 752,423, filed Jul. 5, 1985, and now abandoned, which in turn is a continuation-in-part of patent application Ser. No. 749,161, filed Jun. 26, 1985, now abandoned.

FIELD OF THE INVENTION

This invention relates to aminoglycosides, analogs and derivatives thereof, in the form of phosphate salts as well as the process for making and utilizing same. Aminoglycoside phosphate liposomes and nonguanadino phosphate liposomes, their preparation and use, are particularly described.

BACKGROUND OF THE INVENTION

Aminoglycosides are a class of compounds characterized by the ability to interfere with protein synthesis in micro-organisms. Aminoglycosides consist of two or more amino sugars joined in a glycoside linkage to a hexose (or aminocyclitol) nucleus. The hexose nuclei thus far known are either streptidine or 2-deoxystreptamine, though others may be anticipated. Aminoglycoside families are distinguished by the amino sugar attached to the aminocyclitol. For example, the neomycin family comprises three amino sugars attached to the central 2-deoxystreptamine. The kanamycin and glutamicin families have only two amino sugars attached to the aminocyclitol.

Aminoglycosides include: neomycin B, paromomycin, ribostamycin, lividomycin, kanamycin A, kanamycin B, amikacin, tobramycin, viomycin, gentamicin $C_1$, gentamicin $C_{1a}$, (gentamicin $C_2$, $C_1$, $C_{1a}$ and analogs and derivatives thereof collectively "gentamicin"), sisomicin, netilmicin, streptomycin and dihydrostreptomycin. Streptomycin and dihydrostreptomycin characterized by the presence of a gunadino group are understood to be unique in associating with liposomes in higher drug to lipid ratios than the nonguanadino aminoglycosides. The term "nonguanadino" aminoglycosides will include aminoglycosides other than aminoglycosides bearing a guanadino group.

Unfortunately, use of these compounds has been limited by several factors. Often directed to use in preventing protein synthesis in bacteria, bacteria have demonstrated a remarkable capacity to resist the inhibitory effect of aminoglycosides. Resistance of an organism to aminoglycoside action occurs with a broad range of aminoglycosides. A further problem of aminoglycoside use has been characteristically poor gastric absorption and rapid excretion. Injection of aminoglycosides results in rapid peak plasma concentration often in the neighborhood of 30 to 90 minutes following intramuscular injection which is associated with toxicity. Another limitation is that the aminoglycosides fail to enter the CNS or the eye.

In the therapeutic use of aminoglycosides in animals, including humans, serious problems of toxicity have been noted. For example, therapeutic use in higher animals may be accompanied by ototoxicity potentially involving both auditory and vestibular functions as well as nephrotoxicity, and neuromuscular blockade culminating in respiratory distress.

It is an object of this invention to provide an aminoglycoside in the form of a phosphate salt. It is another object of this invention to provide for aminoglycosides with improved liposomal association. It is a further object of this invention to provide a method of manufacture of liposomes associated with aminoglycoside phosphate. It is another object of this invention that said liposomes substantially associate with said aminoglycoside. It is an additional object of this invention that the liposomes of this invention provide a high aminoglycoside to lipid ratio particularly as to nonguanadino aminoglysocides. It is a further object of this invention to provide such liposomes in a pharmaceutical dosage form for therapeutic treatment of an animal including a human.

SUMMARY OF THE INVENTION

It has now been discovered that aminoglycosides, analogs and derivatives thereof, in the form of phosphate salts, have surprisingly useful therapeutic properties. Aminoglycoside phosphates are found to be particularly adapted to association with liposomes. The phosphate salts of aminoglycosides further may have reduced acute toxicity. The term aminoglycoside will be understood to include analogs and derivatives thereof.

In the past nonguandino aminoglycosides were found to be in rather limited association with liposomes. For example, Morgan et al. "Preparation and Properties of Liposome-Associated Gentamicin" *Antimicrobial Agents and Chemotherapy*, 17:544–548 (1980) reports about 4 mg of gentamicin or less associating with 100 mg of lipid. In the present invention liposomes are associated with enhanced levels of a nonguanadino aminoglycoside frequently at least about 40% of available aminoglycoside. Furthermore, the use of aminoglycoside as a phosphate in making liposomes with enhanced loading efficiency is herein disclosed. This is true for both guanadino and nonguanadino aminoglycosides.

The enhanced association of lipid to nonguanadino aminoglycoside has further enabled the production of liposomes with greater than about 10 milligrams (base equivalent) of nonguanadino aminoglycoside per 100 milligrams of lipid and in a preferred embodiment, greater than about 30 mg of nonguanadino aminoglycoside (base equivalent) per 100 mg of lipid. This permits aminoglycoside liposomes and preparations containing such liposomes to be manufactured at higher potencies.

It is a particular advantage of this invention that enhanced drug to lipid ratio preparations require reduced administration of lipid per drug dosage thus avoiding or reducing toxicity associated with lipid administration.

The enhanced association of available drug with liposomes in the preparation of the liposomes reduces the need for drug and lipid starting materials.

Finally, high potency, pharmaceutical preparations are consequently of smaller volume and thus cause less tissue insult upon administration. This is particularly true as to intramuscular administration.

Methods of preparing and utilizing aminoglycoside phosphate and aminoglycoside phosphate liposomes are described more fully below.

This invention includes liposomes comprising at least one lipid and at least one phosphate salt of an aminoglycoside. This further includes unilamellar and multilamellar vesicles associated with aminoglycosides such as neomycin B, paromomycin, ribostamycin, lividomycin, kanamycin A, kanamycin B, amikacin, tobramycin, gentamicin $C_1$, gentamicin $C_{1a}$, gentamicin $C_2$, netilmicin, streptomycin, dihydrostreptomycin, and sisomicin and phospholipids such as phosphatidylinositol, phosphatidylcholine, phosphatidylethanolamine, phosphatidylserine and phosphatidylglycerol alone or in combination with other lipids. This invention includes the methods of making aminoglycoside phosphate associated liposomes as described below and particularly the liposomes substantially associating with available aminoglycoside phosphate. Also included are nonguanadino aminoglycoside liposomes of greater than about 10 mg and preferably greater than about 30 mg of aminoglycoside per 100 mg of lipid.

Further included in this invention is the method of therapeutic treatment of animals including humans with therapeutically effective amounts of aminoglycoside phosphate, liposomally associated aminoglycoside phosphate, and said phosphate in association with suitable pharmaceutical carrier. Further included is the preparation of the phosphates of aminoglycosides, and particularly the phosphates of neomycin B, paromomycin, ribostamycin, lividomycin, kanamycin A, kanamycin B, amikacin, tobramycin, gentamicin $C_1$, gentamicin $C_{1a}$, gentamicin $C_2$, netilmicin, streptomycin, dihydrostreptomycin, and sisomicin. Additionally included in this invention is aminoglycoside phosphate and liposomally associated aminoglycoside in the treatment of gram-negative pneumonia.

DETAILED DESCRIPTION OF THE INVENTION

Figure 1:
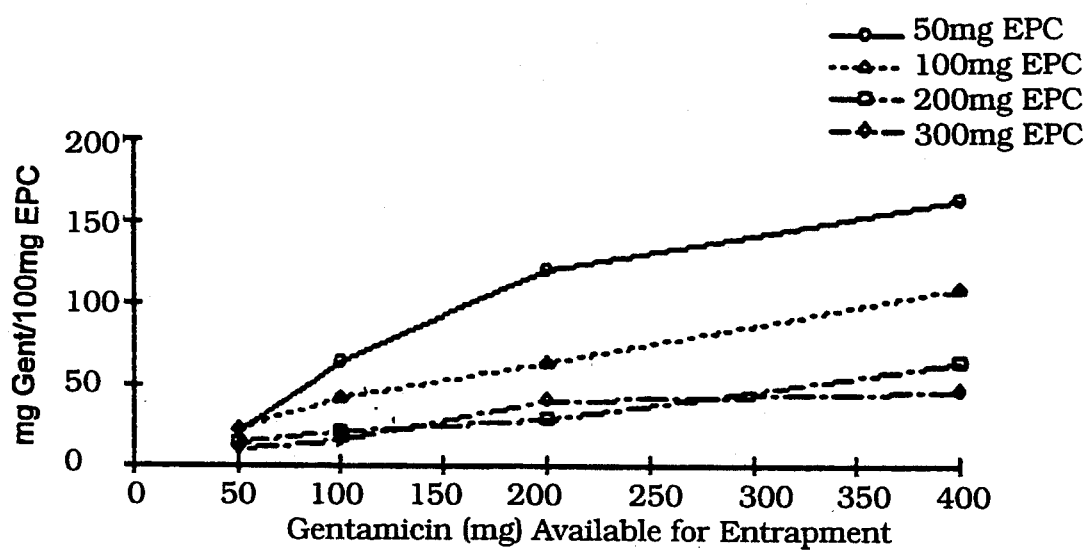
FIG. 1 is a graph of gentamicin phosphate entrapped (mg)/100 mg egg phosphatidylcholine ("EPC") versus gentamicin phosphate (mg) available for entrapment.
Figure 2:
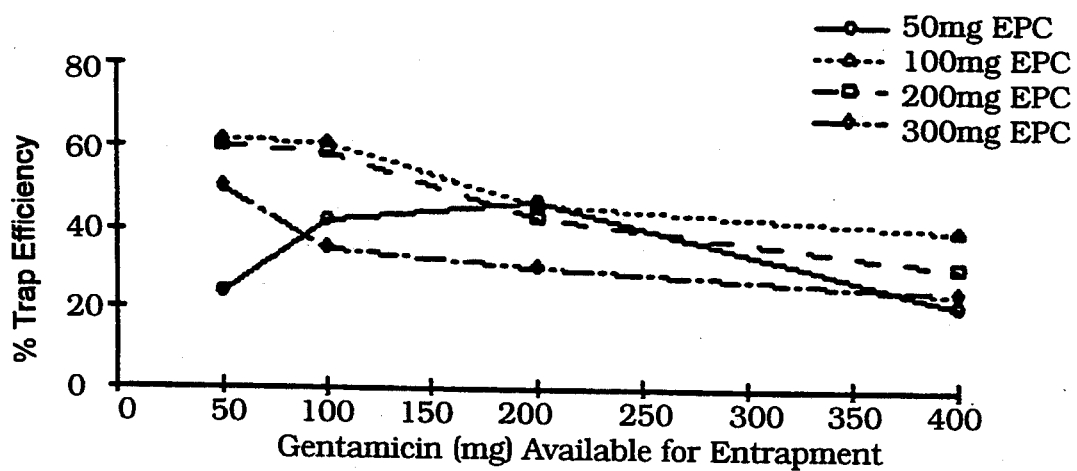
FIG. 2 is a graph of the percentage trapping efficiency versus gentamicin phosphate (mg) available for entrapment.
Figure 3:
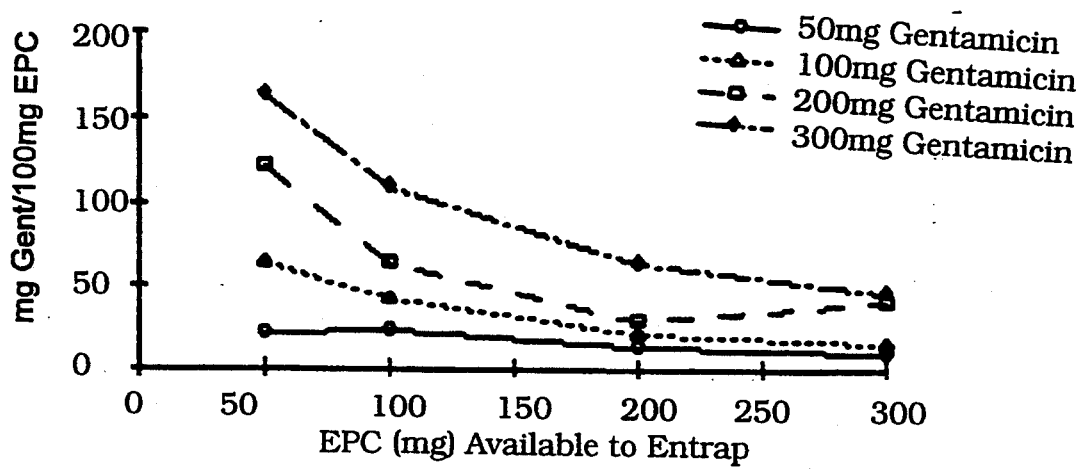
FIG. 3 is a graph of gentamicin phosphate entrapped (mg)/100 mg EPC versus EPC (mg) available to entrap.
Figure 4:
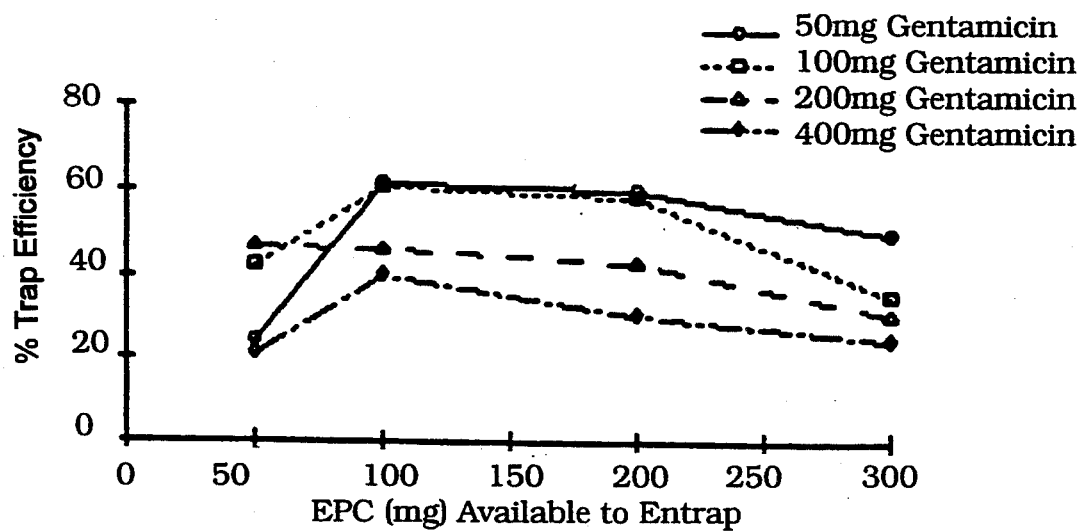
FIG. 4 is a graph of the percentage trapping efficiency versus EPC (mg) available to entrap.

The utility of aminoglycoside containing liposomes is described in connection with the treatment of disease in animals in U.S. Pat. No. 4,552,803 to Lenk et al. The surprisingly increased efficiency of association of aminoglycoside phosphate by liposomes makes these preparations particularly effective and efficient.

It has now been discovered that the aminoglycoside phosphate association with liposomes is enhanced over that of nonphosphate aminoglycosides. For nonguanadino animoglycoside by substantially associated it is to be understood that no more than about 60% of the nonguanadino aminoglycoside present in a liposomal preparation remains free in solution hence unassociated with the liposomes.

Liposomes are vesicles comprising closed bilayer membranes containing an entrapped aqueous phase. Liposomes may be any variety of unilamellar vesicles (possessing a single membrane bilayer) or multilamellar vesicles (e.g. onion-like structures characterized by concentric membrane bilayers, each separated from the next by an aqueous layer).

The liposomes of this invention may be prepared so as to associate with nonguanadino aminoglycoside in ratios equal to or greater than about 10 mg aminoglycoside per 100 mg lipid and as high as about 30 mg nonguanadino aminoglycoside per 100 mg of lipid or higher. The use of aminoglycoside phosphate results in a more concentrated and hence more potent aminoglycoside liposome preparation than would be available with other forms of aminoglycoside.

The liposomes of this invention are formed by methods well known in the art. The original liposome preparation of Bangham et al. (1965, *J. Mol. Biol.* 13:238–252) involves suspending phospholipids in an organic solvent which is then evaporated to dryness leaving a phospholipid film on the reaction vessel. Then an appropriate amount of aqueous phase is added, the mixture is allowed to "swell", and the resulting liposomes which consist of multilamellar vesicles (hereinafter referred to as MLVs) are dispersed by mechanical means. The structure of the resulting membrane bilayer is such that the hydrophobic (nonpolar) "tails" of the lipid orient toward the center of the bilayer while the hydrophilic (polar) "heads" orient towards the aqueous phase. This technique provides the basis for the development of the small sonicated unilamellar vesicles (hereinafter referred to as SUVs) described by Papahadjapoulos and Miller (1967, *Biochim. Biophys. Acta.* 135:624–638) and large unilamellar vesicles (hereinafter referred to as LUVs). The teachings of Bangham and those of Papahadjopoulos are herein incorporated by reference.

In the practice of this invention, a class of liposomes characterized as having substantially equal interlamellar solute distribution is preferred. This preferred class of liposomes is denominated as stable plurilamellar vesicles (SPLV) as defined in U.S. Pat. No. 4,522,803 to Lenk et. al. and includes monophasic vesicles as described in U.S. Pat. No. 4,588,578 to Fountain et. al. and frozen and thawed multilamellar vesicles (FATMLV) as described in "Solute Distributions and Trapping Efficiencies Observed in Freeze-Thawed Multilamellar Vesicles," Mayer et. al., *Biochima et Biophysica Acta.* 817: 193–196 (1985), the teachings of which are herein incorporated by reference.

Large unilamellar vesicles may be modified using an extrusion apparatus by a method described in Cullis et al., U.S. patent application Ser. No. 788,017, filed Oct. 16, 1985 and now abandoned, entitled "Extrusion Technique for Producing Unilamellar Vesicles", (LUVETs) incorporated herein by reference. To make LUVET vesicles by this technique, MLVs are extruded under pressures of up to about 700 psi through a membrane filter. These vesicles may be exposed to at least one freeze and thaw cycle prior to the extrusion technique; this procedure is described in Bally et al., U.S. patent application Ser. No. 800,545, filed Nov. 21, 1985 and now abandoned, entitled "Multilamellar Liposomes Having Improved Trapping Efficiencies", incorporated herein by reference.

Another technique that is used to prepare vesicles is one which forms reverse-phase evaporation vesicles (REV), Papahadjopoulos et al., U.S. Pat. No. 4,235,871, incorporated herein by reference.

The term lipid as used herein shall mean any suitable material resulting in a bilayer such that a hydrophobic portion of the lipid material orients toward the bilayer while a hydrophilic portion orients toward the aqueous phase.

Two general classes of lipid compounds are useful in the present invention. The most prominent members are highly hydrophobic compounds, such as triglycerides. Corn oil serves as a convenient and economical source of mixed triglycerides, but other vegetable oils, including but not limited to palm kernel oil, coconut oil, soybean oil, sunflower oil, safflower oil, cocoa butter, and the like may be used. Specific molecular species might be employed as well. Such species may include, but are not limited to, trilaurin, trimyristin, tripalmitin and tristearin, or other glyceryl esters in which the fatty acyl chains of these compounds as well as other fatty acids are incorporated in a non-homogeneous fashion. Other broad classes of long chain hydrophobic compounds such as the wide range of cholesterol esters may be used. It has even been found that long chain organic mixtures such as petroleum jelly are acceptable lipid materials.

A variety of cholesterols and other sterols and their water soluble derivatives have been used to form liposomes; see specifically Janoff et al., U.S. patent application Ser. No. 773,429, filed Sep. 10, 1985 entitled "Steroidal Liposomes". Mayhew et al., WO 85/00968, published Mar. 14, 1985, describes a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., U.S. patent application Ser. No. 786,740, filed Oct. 15, 1986 and now abandoned, entitled "Alpha-Tocopherol-Based Vesicles" and incorporated herein by reference. Preferred of this group are cholesterol hemisuccinate and tocopherol hemisuccinate. The only constraint appears to be that the hydrophobic compounds selected should, when uncomplexed with the other components of this invention, be soluble in a particular organic solvent chosen for use in the manufacture of the liposomes.

The second broad class of lipid materials used in this invention are amphipathic in character. Hydrophilic character could be imparted to the molecule through the presence of phosphato, carboxylic, sulphato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group. The preferred amphipathic compounds are phosphoglycerides, representative examples of which include phosphatidylcholine, phosphatidylethanolamine, lysophosphatidylcholine, lysophosphatidylethanolamine, phosphatidylserine, phosphatidylinositol, phosphatidic acid, dimyristoylphosphatidylglycerol and diphosphatidylglycerol alone or in combination with other lipids. Synthetic saturated compounds such as dimyristoylphosphatidylcholine, dipalmitoylphosphatidylcholine, or distearoylphosphatidylcholine or unsaturated species such as dioleoylphosphatidylcholine or dilinoleoylphosphatidylcholine might also be usable. Other compounds lacking phosphorous, such as members of the sphingolipid and glycosphingolipid families, are also within the group designated as lipid.

A method for preparing the sterol containing liposomes involves adding to an aqueous buffer a salt form of an organic acid derivative of a sterol capable of forming closed bilayers in an amount sufficient to form completely closed bilayers which entrap an aqueous compartment. A suspension of multilamellar vesicles is formed by shaking the mixture. The formation of vesicles is facilitated if the aqueous buffer also contains the counterion of the salt in solution.

The application of energy to the suspension, e.g., sonication, or extrusion of the vesicles through a French pressure cell (French Press) or through a porous filter of the appropriate pore size, will convert the multilamellar sterol vesicles to unilamellar vesicles.

Liposomes entrap an aqueous medium which is enclosed by the lipid bilayers. The aqueous medium can be for example, water or water containing a dissolved salt or buffer. Examples of such salts or buffers can be sodium chloride and phosphate buffered saline (PBS). Other buffers include but are not limited to borate, citrate, Tris-HCl(Tris-(hydroxymethyl)-aminomethane hydrochloride), and HEPES (N-2-hydroxyethyl piperazine-$N^1$-2-ethane sulfonic acid). Buffers may be in the pH range of between about 2.0 and about 14.0. In the preferred embodiment, the preparations are hydrated with HEPES buffer (150 mM NaCl, 20 mM HEPES), pH 7.0, borate buffer (100 mM $Na_2HCO_3$, 50 mM $H_3BO_3$, pH 8.5, or citrate buffer (150 mM Na-citrate), pH 8.5.

In a liposome-drug delivery system, the therapeutic agent, here aminoglycoside, is entrapped in the liposome and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179, Lenk, et al., U.S. Pat. No. 4,522,803, and Fountain et al., U.S. Pat. No. 4,588,578.

Optionally, the liposomes can be dehydrated, thereby enabling storage for extended periods of time until use. Standard freeze-drying equipment or equivalent apparatus may be used to dehydrate the liposomes. Liposomes may also be dehydrated simply by placing them under reduced pressure. Alternatively, the liposomes and their surrounding medium can be frozen in liquid nitrogen prior to dehydration. Dehydration with prior freezing may be performed in the presence of one or more protective sugars in the preparation, according to the process of Janoff et al., U.S. patent application Ser. No. 759,419, filed Jul. 26, 1985 and now abandoned, entitled "Dehydrated Liposomes", incorporated herein by reference. Examples of protective sugars that may be used include, but are not limited to, trehalose, maltose, sucrose, glucose, lactose and dextran. Alternatively, multilamellar vesicles may be dehydrated with prior freezing without protective sugars. When the dehydrated liposomes are to be used, rehydration is accomplished by methods which include simply adding an aqueous solution, e.g., distilled water, to the liposomes and allowing them to rehydrate.

The aminoglycosides of this invention are administered associated with liposomes, and if desired, in admixture with a pharmaceutically-acceptable carrier (such as physiological saline or phosphate buffer) selected with regard to the intended route of administration and standard pharmaceutical practice. Dosages for aminoglycosides when associated with liposomes will often be about that of the aminoglycoside alone; dosages will be set by the prescribing medical professional considering many factors including the age, weight and condition of the patient. The ratio of active ingredient to carrier will naturally depend on the chemical nature, solubility and stability of the aminoglycoside, as well as the dosage contemplated. For parenteral administration or injection via such routes as intravenous, intraperitoneal, intramuscular, subcutaneous, or intra-mammary route, sterile solutions of the liposome composition are prepared. For intravenous use, the total concentration of solutes should be controlled to render the preparation isotonic.

In another example of their use, liposomal associated aminoglycosides may be incorporated into a broad range of topical dosage forms including but not limited to gels, oils, emulsions and the like. For instance, the suspension containing the liposomal associated aminoglycoside may be added to the aqueous phase as an ingredient in the liposome preparation. Such preparations may be administered as topical creams, pastes, ointments, gels, lotions and the like for direct application.

1. Phosphate salts of aminoglycosides

The aminoglycosides each contain one or more amino sugars linked by glycosidic linkages to a basic six-membered carbon ring. Various phosphate salts may be formed by titration with acids having phosphate groups. In general it is easier to form a phosphate salt of an aminoglycoside than link a phosphate to an aminoglycoside covalently.

For example, gentamicin base contains five titratable amino groups.

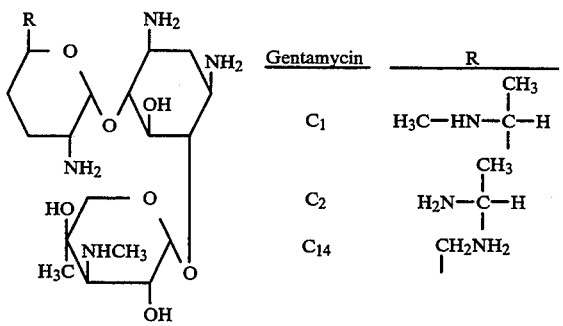

Depending on a number of factors including the choice of titrant, specific aminoglycoside, solvent and temperature, a number of phosphate salts are theoretically possible.

| Titrant | Salt* |
|---|---|
| $H_3PO_4$ | $Gent_3(H_3PO_5)_5$ |
| $NaH_2PO_4$ | $Gent_2(H_2PO_4)_5Na_5$ |
| $Na_2HPO_4$ | $Gent(HPO_4)_5Na_{10}$ |

*Gent = gentamicin base

Clearly, aminoglycosides, having the ability to associate with a number of phosphate moieties, may be utilized in degrees of phosphate association. However, in the practice of this invention, the preferred aminoglycosides will have a ratio of from about 1:1.6 to about a ratio of 1:5 molecules of aminoglycoside to phosphate. As used herein aminoglycoside phosphate will refer to an aminoglycoside associated with at least one phosphate.

2. Preparation of Phosphate Form of Gentamicin

Gentamicin phosphate is a preferred aminoglycoside phosphate of this invention. Gentamicin base was prepared from gentamicin sulfate as described below, and subsequently converted to a phosphate by titration with phosphoric acid to a pH sufficiently low to cause the phosphate to associate with the aminoglycoside. Usually a pH of about 2.5 will be suitable.

In general aminoglycoside phosphate may be prepared with any solvent that adequately solubilizes both aminoglycoside and phosphate but is not appreciably acidic. Aqueous solvents, particularly water, are preferred. The pH present will be characteristic of the source of phosphate titrant and the aminoglycoside. Sources of phosphate are phosphoric acids and metal phosphate salts such as sodium or potassium phosphate. The temperature and pressure are not critical and standard temperature and pressure are often most convenient. The temperature should not exceed a temperature at which the aminoglycoside remains stable.

3. Preparation of Aminoglycoside Phosphate Liposomes

Liposomes may be prepared by any of a number of the methods disclosed in the above incorporated references. Alternatively a method of making liposomes by the process of mixing an aqueous phase with lipid free of organic solvent may be employed. Monophasic vesicles (MPVs) as described in U.S. Pat. No. 4,588,578 are formed by the general method of (a) forming a dispersion of lipid in an organic solvent, (b) combining the dispersion with an aminoglycoside phosphate in an aqueous phase to form a biphasic mixture in which the aqueous phase can be encapsulated, and (c) removing the organic solvent.

More specifically, a lipid or a mixture of lipids and an aqueous component are added to an organic solvent or a combination of organic solvents in amounts sufficient to form a monophase. The solvent or solvents are evaporated until a film forms. Then an appropriate amount of aqueous component is added, and the film is resuspended and agitated in order to form the MPVs.

The organic solvent or combination of solvents used in the process must be miscible with water and once mixed with water should solubilize the lipids used to make the MPVs.

For example, an organic solvent or mixture of solvents which satisfies the following criteria may be used in the proceeds: (1) 5 ml of the organic solvent forms a monophase with 0.2 ml of aqueous component and (2) the lipid or mixture of lipids is soluble in the monophase.

Solvents which may be used in the process of the present invention include but are not limited to ethanol, acetone, 2-propanol, methanol, tetrahydrofuran, glyme, dioxane, pyridine, diglyme, 1-methyl-2-pyrrolidone, butanol-2, butanol-1, isoamyl alcohol, isopropanol, 2-methoxyethanol, or a combination of chloroform and methanol (e.g., in a 1:1 ratio v/v).

The evaporation of solvent should be accomplished at suitable temperatures and pressures which maintain the monophase and facilitate the evaporation of the solvents. In fact, the temperatures and pressures chosen are not dependent upon the phase-transition temperature of the lipid used to form the MPVs. The advantage of this latter point is that heat labile aminoglycosides which have desirable properties can be incorporated in MPVs prepared from phospholipids such as distearoylphosphatidylcholine, which can be formed into conventional liposomes only at temperatures above the phase-transition temperature of the phospholipids.

Stable plurilamellar vesicles, SPLVs, are prepared as follows: An amphipathic lipid or mixture of lipids is dissolved in an organic solvent. Many organic solvents are suitable, but diethyl ether, fluorinated hydrocarbons and mixtures of fluorinated hydrocarbons and ether are preferred. To this solution are added an aqueous phase and the aminoglycoside to be entrapped. This biphasic mixture is converted to SPLVs by emulsifying the aqueous material within the solvent while evaporating the solvent. Evaporation can be accomplished during sonication by any evaporative technique, e.g., evaporation by passing a stream of inert gas over the mixture, by heating, or by vacuum. The volume of solvent used must exceed the aqueous volume by a sufficient amount so that the aqueous material can be completely emulsified in the mixture. In practice, a minimum of roughly 3 volumes of solvent to 1 volume of aqueous phase may be used. In fact the ratio of solvent to aqueous phase can vary to up to 100 or more volumes of solvent to 1 volume aqueous phase. The amount of lipid must be sufficient so as to exceed that amount needed to coat the emulsion droplets (about 40 mg of lipid per ml of aqueous phase). The upper boundary is limited only by the practicality and efficiency, as for example, SPLVs can be made with 15 gm of lipid per ml of aqueous phase.

The process produces liposomes with different supermolecular organization than conventional liposomes. According to the present invention, the entire process can be performed at a temperature range of about 4°–60° C. regardless of the phase transition temperature of the lipid used. The advantage of this latter point is that heat labile aminoglycosides which have desirable properties can be incorporated in SPLVs prepared from phospholipid such as distearoylphosphatidylcholine, but can be formed into conventional liposomes only at temperatures above their phase-transition temperature.

To form FATMLVs one example of a suitable process is as follows: one or more selected lipids are deposited on the inside walls of a suitable vessel by dissolving the lipids in an organic solvent such as chloroform and then evaporating the organic solvent, adding an aqueous phase containing aminoglycoside which is to be encapsulated to the vessel, allowing the aqueous phase to hydrate the lipid, and mechanically agitating (for example, by swirling or vortexing) the resulting lipid suspension to produce the liposomes which are then subjected to a freeze-thaw process.

Alternatively, one or more selected lipids can be dispersed by employing mechanical agitation in an aqueous phase to produce multilamellar vesicles (MLVs) which also may be subjected to the freeze-thaw process. The process requires about 1–10 minutes at a temperature above the gel/liquid crystalline transition temperature.

The lipid concentration for producing MLVs is at least about 50 mg/ml aqueous solvent. At lower concentrations, multilamellar vesicles having a high trapping efficiency are more difficult to form. A preferred lipid concentration is between about 100 and 1000 mg/ml aqueous solvent, more preferably 100–600 mg/ml, and still more preferably 100–400 mg/ml. Neither detergent nor organic solvent is required.

The freeze-thaw cycle that results in FATMLVs requires rapid freezing of the dispersed liposome mixture and then warming the frozen mixture in a constant temperature bath, to a temperature which will cause the aqueous phase to melt. The temperature employed is generally above the transition temperature for the gel/liquid crystalline transition. A constant temperature bath of about 25°–50° C., preferably about 40° C., is generally effective.

Liquid nitrogen baths have been found to be particularly effective for the freezing step. The number of freeze-thaw cycles affects the properties of the resulting FATMLV. Generally, three or more preferrably about five or more freeze-thaw cycles are required to obtain an equilibrium interlamellar osmotic balance. About five freeze-thaw cycles in liquid nitrogen and a 40° C. constant temperature bath, result in preferred FATMLV's.

4. Pharmacological Use of Aminoglycosides

The aminoglycosides may be classified as broad spectrum antibiotics. With respect to antibacterial spectrum, there are similarities among them, but there are also considerable differences, hence generalizations should be avoided. The aminoglycosides of this invention and liposomally associated aminoglycosides are useful in therapeutically-effective doses in the treatment of gram-negative pneumonia.

Aminoglycosides may be administered in combination with one or more pharmaceutically acceptable carriers. Such carriers are well known in the art. Aminoglycosides are preferably administered intramuscularly or intravenously. Ophthalmic solutions and ointments are also available for topical ophthalmic applications. Creams are available in some cases for topical application.

Gentamicin (base equivalent) for example, may be administered IM or IV at about 1 to 1.7 mg/kg of body weight about every eight hours or 0.75 to 1.25 mg/kg every six hours for about seven to ten days. However, many considerations are involved in determing an actual dosage including incidence of renal failure, the aminoglycoside in use, the animal and its presenting condition. A therapeutically effective dose of an aminoglycoside will be that dosage which, in view of the specifics of the application, produce the desired result. IM or IV preparations of aminoglycoside phosphate associated liposomes are preferably administered suspended in a saline solution.

EXAMPLE 1

Gentamicin Phosphate

In this conversion, 200 mg of gentamicin base was dissolved in 1 ml water. This was then titrated to the equivalence point. For $H_3PO_4$ 85% (weight:volume) the equivalence point was pH 2.5. The reaction was performed at standard temperature and pressure.

If required, gentamicin base can be prepared from gentamicin sulfate by ion exchange chromatography. The anion exchanger resins such as AG1-XB (hydroxide form) (BioRad) is slurried in distilled, deionized water (dH20). A column, conveniently 2.6 cm ID×33 cm, was poured according to the manufacturer's instructions and washed with sufficient $H_2O$. In the current example, two column volumes of dH20 was sufficient, but each apparatus will have unique requirements well known by those skilled in the art. Gentamicin sulfate in dH20 was applied to the column at a moderate flow rate. One hundred ml of a 200 mg/ml solution of gentamicin sulfate and a flow rate of 50 ml/hr is convenient. The column was then washed with dH20. Fractions were collected, and those containing gentamicin were pooled and lyophilized. The potency of the base may be determined by any of a number of techniques including by bioassay and by spectrophotometric determination of trinitrobenzyl adduct(s) of the drug substance. The base was converted to a phosphate by aqueous titration with phosphoric acid and sodium phosphate buffer.

EXAMPLE 2

Preparation of Aminoglycoside Phosphate Liposomes

Preparation of Precursor Liposomes at Various Gentamicin Concentrations 16 roundbottom flasks were set up in groups of four. Each group contained four flasks containing 50, 100, 200, and 300 mg of lipid such as egg phosphatidylcholine (EPC), either as a thin film or in powdered form. The vesicles in Group 1 were made with 50 mg/ml aminoglycoside (in all groups here, gentamicin). First, 1.0 ml aliquots of 50 mg/ml aminoglycoside were pipetted into the four separate flasks that made up this group and they were vortexed vigorously. Complete mixing yielded MLV preparations that were homogeneous and had a milky consistency. These samples were transferred to plastic cryovials. The samples then underwent the freeze-thaw process. This process was repeated for the three remaining groups.

The samples in Group 2 were made with 100 mg/ml of aminoglycoside, and the same four starting weights of EPC. Likewise, the four samples in Group 3 were made with 200 mg/ml aminoglycoside, and the four samples in Group 4 were made with 400 mg/ml of aminoglycoside. The resulting set of 16 samples were arranged in groups of four and each contained a different starting proportion of lipid and aminoglycoside.

Freeze-thaw cycle

The aminoglycoside:lipid mixtures were transferred to the cryovials, which were then capped. It was, however, helpful that the cryovial seal allow for the expanding and contracting gasses to vent during freezing and thawing. Each vial was secured on a metal extender used to dip the vial in a liquid nitrogen tank.

Each sample was vortexed vigorously to mix the lipid with the aqueous aminoglycoside. The vial was immediately plunged into a liquid nitrogen container. To enhance drug-lipid interactions, the samples were thoroughly mixed and had a homogeneous, milky consistency upon freezing.

When a sample was completely frozen (approximately one minute), the vial was transferred to a 40° C. water bath, and allowed to thaw completely. After thawing, the vials were vortexed vigorously and then immediately started in the next freeze-thaw cycle by plunging the vial back into the liquid nitrogen before the phases had a chance to separate.

A minimum of about five freeze-thaw cycles was required for best results; however, the entrapment of certain compounds has been shown to increase by increasing the number of freeze-thaw cycles to about ten.

The results of the foregoing procedure using gentamicin phosphate are shown in FIGS. 1 through 4. For various aminoglycoside phosphates, this procedure may be useful in determining optimal concentrations of aminoglycoside and optimal aminoglycoside:lipid ratios. The weights of gentamicin phosphate are reported in mass of active agent without reference to weight of the phosphate counter ion unless otherwise noted.

EXAMPLE 3

Figure 5:
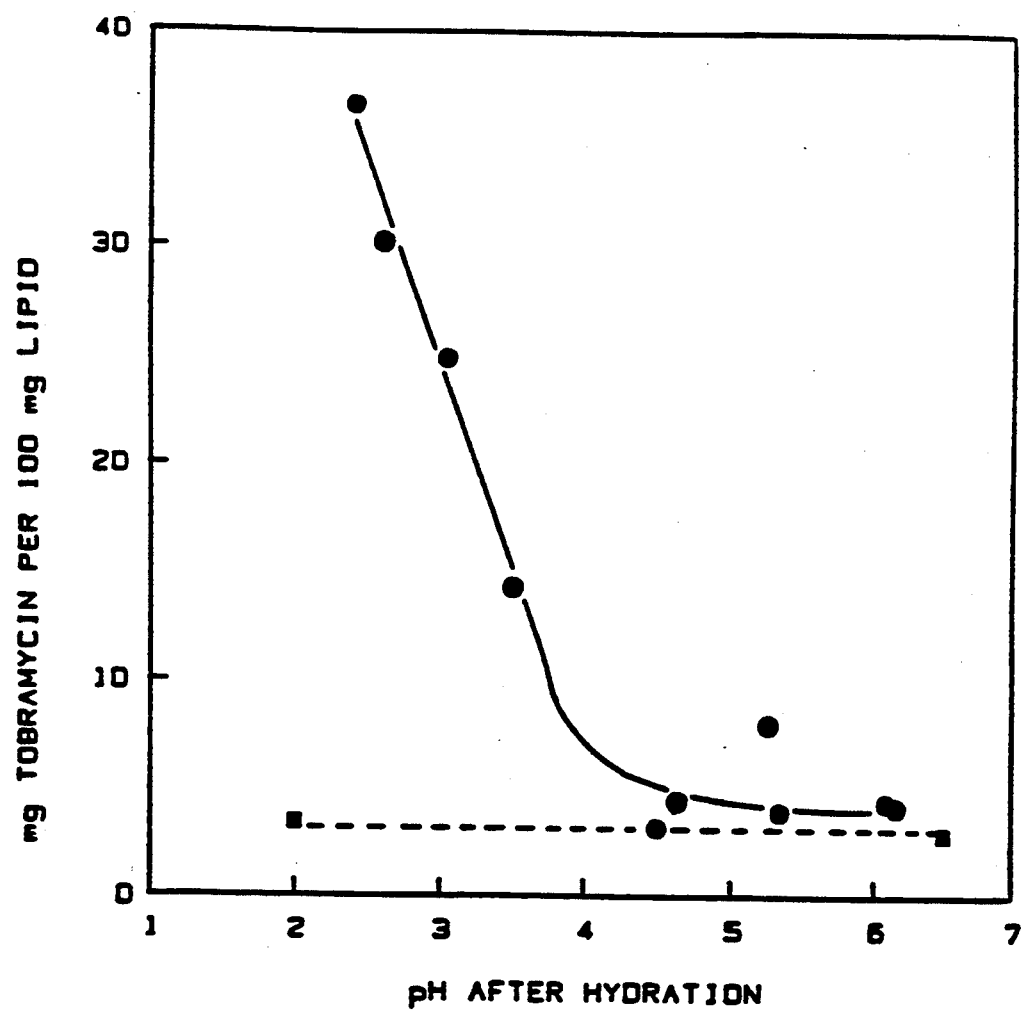
FIG. 5 is a graph of the comparative liposomal entrapment of aminoglycoside sulfate and phosphate.

Comparative Liposomal Entrapment of Nonguanadino Aminoglycoside Sulfate and Aminoglycoside Phosphate A) Tobramycin As may be seen from FIG. 5, liposomal association of tobramycin in the form of a phosphate was far more efficient than tobramycin in the form of a sulfate. Tobramycin samples (100 mg in a total volume of 0.5 ml) were adjusted to the appropriate pH with phosphoric acid (FIG. 5, marked with solid circles) or sulfuric acid (FIG. 5, marked with solid squares). The tobramycin was them added to egg phosphatidylcholine according to the freeze-thaw method of Example 2 utilizing 10 freeze-thaw cycles. The results clearly indicate that it is not merely the pH of the aminoglycoside containing aqueous phase that results in greater associate efficiency. Tobramicin phosphate over the entire pH range shown in FIG. 5 is more liposomally associated than tobramycin sulfate. As the tobramicin is titrated with phosphoric acid phosphate association increases as does liposomal association. At pH of 2.5, trapping efficiencies for tobramycin phosphate exceeded or far exceeded 35% yielding liposome dispersions having a tobramycin phosphate concentration of about 0.35 mg per mg of EPC.

B) Amikacin

A comparative test of the liposomal association of amikacin-$SO_4$ and amikacin-$PO_4$ at pH 2.0 was performed. To form the sulfate, the free base of amikacin in phosphate buffered saline was titrated to pH 2.0 with $H_2SO_4$. To form the phosphate, amikacin in phosphate buffered saline was titrated to pH 2.0 with 85% $H_3PO_4$ (weight/volume). Amikacin association was compared at about 10, 37, 50 and 80 mg. Liposomes were then prepared by the SPLV method of Lenk et al. U.S. Pat. No. 4,522,803. Amikacin/liposomal association was determined by spectrophotometric assay and was in each instance at least about ⅓ greater for the amikacin phosphate salt form than for the amikacin sulfate form.

The foregoing examples are merely illustrative of the invention and in no way limiting. Other examples will be immediately obvious to those skilled in the art. The invention will be limited only by the claims.

We claim:

1. Liposomes comprising at least one phoshate salt of an aminoglycoside and a lipid bilayer comprising a lipid, wherein the ratio of the aminoglycoside to the lipid (weight/weight) is at least about 1:10.

2. The liposomes of claim 1 wherein said liposomes are unilamellar.

3. The liposomes of claim 1 wherein said liposomes are multilamellar.

4. The liposomes of claim 1 wherein said aminoglycoside is neomycin B, paromomycin, ribostamycin, lividomycin, kanamycin A, kanamycin B, amikacin, tobramycin, gentamicin $C_1$, gentamicin $C_{1a}$, gentamicin $C_2$, netilmicin, streptomycin, dihydrostreptomycin, or sisomicin.

5. The liposomes of claim 4 wherein said aminoglycoside is a gentamicin.

6. The liposomes of claim 4 wherein said aminoglycoside is tobramicin.

7. The liposomes of claim 4 wherein said aminoglycoside is a amikacin.

8. The liposomes of claim 4 wherein said aminoglycoside is streptomycin.

9. The liposome of claim 1, wherein the lipid is a phospholipid.

10. The liposome of claim 9 wherein the phospholipid is phosphatidylinositol, phosphatidylcholine, phosphatidylethanolamine, phosphatidylserine or phosphatidylglycerol.

11. The liposome of claim 10 wherein the phospholipid is phosphatidylcholine.

12. A method of preparing a composition comprising at least one phosphate salt of an aminoglycoside in association with a liposome comprising the steps of:
(a) dispersing an aminoglycoside phosphate in an aqueous phase; and
(b) combining said aqueous phase with a lipid under conditions adapted to the formation of a liposome comprising said lipid and adapted to the association of said aminoglycoside with said lipid in said liposome, wherein the ratio of the aminoglycoside to the lipid in the liposome (weight/weight) is at least about 1:10.

13. The method of claim 12 wherein the aminoglycoside phosphate is neomycin B, paromomycin, ribostamycin, lividomycin, kanamycin A, kanamycin B, amikacin, tobramycin, gentamicin $C_1$, gentamicin $C_{1a}$, gentamicin $C_2$, netilmicin, streptomycin, dihydrostreptomycin, or sisomicin.

14. The method of claim 13 wherein the aminoglycoside is a gentamicin phosphate.

15. A method of treating animals, including humans, comprising administration of a therapeutically effective amount of an aminoglycoside phosphate salt wherein said aminoglycoside phosphate salt is associated with a liposome, wherein the liposome comprises a lipid bilayer comprising a lipid and wherein the ratio of the aminoglycoside phosphate to the lipid in the liposome (weight/weight) is at least about 1:10.

16. The method of claim 15 wherein the aminoglycoside is gentamicin.

17. The method of claim 15 in the treatment of gram-negative pneumonia.

* * * * *